United States Patent [19]

Kleiner et al.

[11] 4,196,141
[45] Apr. 1, 1980

[54] BISPHOSPHINIC ACID ANHYDRIDES AND PROCESS FOR THEIR PREPARATION

[75] Inventors: Hans-Jerg Kleiner, Kronberg; Walter Dürsch; Fritz Linke, both of Königstein, all of Fed. Rep. of Germany

[73] Assignee: Hoechst Aktiengesellschaft, Frankfort am Main, Fed. Rep. of Germany

[21] Appl. No.: 10,065

[22] Filed: Feb. 7, 1979

Related U.S. Application Data

[62] Division of Ser. No. 913,043, Jun. 6, 1978, abandoned.

[30] Foreign Application Priority Data

Jun. 11, 1977 [DE] Fed. Rep. of Germany ....... 2726479

[51] Int. Cl.$^2$ .............................................. C07F 9/30
[52] U.S. Cl. ................................ 260/545 P; 260/932; 260/934
[58] Field of Search ..................................... 260/545 P

[56] References Cited

U.S. PATENT DOCUMENTS

| | | | |
|---|---|---|---|
| 3,639,473 | 2/1972 | Venezky | 260/545 P |
| 3,689,548 | 9/1972 | Maier | 260/545 P |

FOREIGN PATENT DOCUMENTS 193508  3/1967  U.S.S.R. ............... 260/545 P

OTHER PUBLICATIONS

Michaelis et al., "Ber," Jahreg VII, p. 1070 (1874).
Kosolapoff et al., "J.A.C.S." 73:4101 (1951).
Moedritzer, "J.A.C.S.," 83:4381 (1961).

*Primary Examiner*—N. Morgenstern
*Attorney, Agent, or Firm*—Connolly and Hutz

[57] ABSTRACT

Bisphosphinic acid anhydrides of the formula

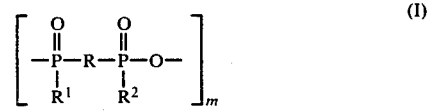

in which R is a saturated open chain or cyclic alkylene radical, an arylene or aralkylene radical, and $R^1$ and $R^2$, which may be identical or different, represent optionally halogen substituted alkyl, aryl or aralkyl radicals, and m represents an integer $\geq 1$, preferably $\geq 2$ and a process for their preparation which comprises reacting bisphosphinic acid derivatives of the formula

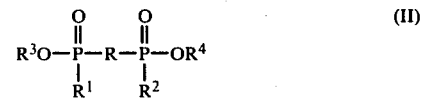

in which $R^3$ and $R^4$, are hydrogen, monovalent cations, the ammonium group or optionally halogen-substituted alkyl groups, with inorganic acid chlorides and/or with phosgene and/or with oxalyl chloride and/or with the corresponding bromine compounds in a molar ratio of about 1:1 at a temperature up to 250° C.

4 Claims, No Drawings

BISPHOSPHINIC ACID ANHYDRIDES AND PROCESS FOR THEIR PREPARATION

This application is a division of application Ser. No. 913,043 filed June 6, 1978 abandoned.

Alkane-phosphinic acid anhydrides of the formula R'R''P(O)—O—P(O)R'R'', in which R' and R'' represent alkyl, aryl or aralkyl groups, have already been known. They can be obtained, for example, by reacting alkane-phosphinic acids or alkane-phosphinic acid esters with phosgene (German Offenlegungsschrift No. 21 29 583).

With the attempt to apply this reaction also to the preparation of other phosphinic acid anhydrides it has now been found that bisphoshinic acid anhydrides, too, can be prepared in an excellent manner by reacting the free bisphosphinic acids, their salts and/or esters with inorganic acid chlorides, phosgene or oxalyl chloride.

The present invention relates to bisphosphinic acid anhydrides of the formula

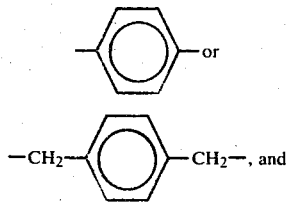

in which R is a saturated, open-chain branched or unbranched alkylene radical having from 1 to 10, preferably from 1 to 6 carbon atoms,

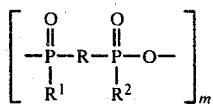

$R^1$ and $R^2$ represent identical or different alkyl groups having from 1 to 4, preferably from 1 to 2 carbon atoms.

Those bisphosphinic acid anhydrides are preferred wherein R is a saturated unbranched alkylene group having from 1 to 10 carbon atoms, preferably from 1 to 6 carbon atoms and $R^1$ has the same meaning as $R^2$.

A further subject of the invention is a process for the preparation of bisphosphinic acid anhydrides of the formula

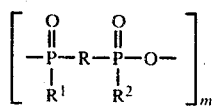

in which R is a saturated open chain or cyclic alkylene radical, an arylene or aralkylene radical,
and $R^1$ and $R^2$, which may be identical or different, represent optionally halogen-substituted alkyl, aryl or aralkyl radicals, and
m represents an integer $\geq 1$, preferably $\geq 2$, which comprises reacting bisphosphinic acid derivatives of the formula

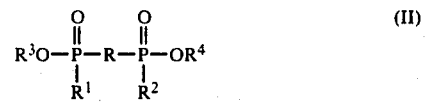

in which R, $R^1$ and $R^2$ are defined as in formula I, and $R^3$ and $R^4$, which may be identical or different, represent hydrogen, monovalent cations, the ammonium group or optionally halogen-substituted alkyl groups, with inorganic acid chlorides and/or with phosgene and/or with oxalyl chloride and/or with the corresponding bromine compounds in a molar ratio of about 1:1 at a temperature of from room temperature (about 20° C.) to 250° C., preferably from about 100° to 200° C., optionally in the presence of inert solvents.

As saturated open-chain or cyclic alkylene radicals R in formulae I and II there may be mentioned all types of branched and unbranched and cyclic alkylene radicals, for example —CH$_2$—, —CH$_2$—CH$_2$—, (—CH$_2$—)$_3$, —(CH$_2$)$_4$—,

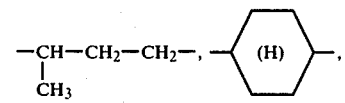

etc.; preference is given to saturated open-chain branched or unbranched alkylene radicals having from 1 to 10, preferably from 1 to 6 carbon atoms, the linear alkylene radicals being particularly advantageous.

As arylene radicals R there are mentioned, for example, the phenylene and naphthylene radicals, the p-phenylene radical being preferred.

Aralkylene radicals are, for example, the tolylene radical, the xylylene radical, etc., of which the p-xylylene radical represents the preferred radical.

It goes without saying that all radicals that may stand for R can also carry substituents which are slow to react, for example halogen-substituents.

As optionally halogen-substituted alkyl radicals $R^1$ and $R_2$, which may be identical or different, there are mentioned for example the following compounds: CH$_3$, C$_2$H$_5$, n—C$_3$H$_7$, i—C$_4$H$_9$, n—C$_{10}$H$_{21}$, CH$_2$Cl, C$_2$H$_4$Br, etc., preference is given to (unsubstituted) alkyl groups having from 1 to 4, especially 1 to 2 carbon atoms. As aryl and aralkyl radicals $R^1$ and $R^2$ there may be mentioned, for example, the phenyl, naphthyl, benzyl radicals, etc. In compounds I and II the radicals $R^1$ and $R^2$ are preferably the same. m represents in formula I an integer of at least 1, preferably at least 2. As monovalent cations for the radicals $R^3$ and $R^4$ in formula II there are to be mentioned first of all the alkali metal ions, especially Na and K ions; if $R^3$ and $R^4$ represent optionally halogen-substituted alkyl groups, there may be mentioned above all alkyl groups of from 1 to 5 carbon atoms which may also carry from 1 to 3 halogen atoms, especially chlorine atoms, as substituents. $R^3$ and $R^4$ are preferably the same.

As bisphosphinic acid derivatives of the formula II which are used as starting compounds for the process of the invention, there may be mentioned, for example: Methane-bis-methylphosphinic acid-methyl ester, methane-bis-methylphosphinic acid-ethyl ester, methane-bis-methylphosphinic acid-isopropyl ester, ethane-1,2-bis-(methylphosphinic acid-butyl ester), ethane-1,2-bis(-methylphosphinic acid-amyl ester), ethane-1,2-bis- (ethylphosphinic acid-ethyl ester), ethane-1,2-bis-(methylphosphinic acid-2-chloro-ethyl ester), ethane-1,2-bis-(butylphosphinic acid-methyl ester), butane-1,4-bis-(methyl-phosphinic acid-butyl ester), hexane-1,6-bis-(methylphosphinic acid-butyl ester), decane-1,10-bis-(methylphosphinic acid-isobutyl ester), butane-1,4-bis-(methylphosphinic acid)-monobutyl ester, methane-bis-(methylphosphinic acid), ethane-1,2-bis-(methylphosphinic acid), propane-1,3-bis-(methylphosphinic acid), butane-1,4-bis-(ethylphosphinic acid), hexane-1,6-bis-(methylphosphinic acid), decane-1,10-bis-(methylphosphinic acid), cyclohexane-1,4-bis-(methylphosphinic acid), p-phenylene-bis-(ethylphosphinic acid), p-xylylene-bis-(chloromethyl-phosphinic acid), as well as the sodium, potassium and ammonium salts of the above-mentioned acids. These compounds may be prepared according to known processes; the ethane-1,2-bis-(alkylphosphinic acid-alkyl esters), for example, can easily be prepared technically according to the process of German Offenlegungsschrift No. 23 02 523. From these esters and analogous forms the corresponding acids may be prepared, preferably according to the methods described in German Pat. Nos. 24 41 783 and 24 41 878. The inorganic acid chlorides used as reaction components are preferably thionyl chloride and phosphorus pentachloride.

These acid chlorides as well as the phosgene and the oxalyl chloride may be used individually as well as in a mixture. It is also possible to use the corresponding bromine compounds, i.e. thionyl bromide, phosphorus pentabromide, COBr$_2$, oxalyl bromide, etc., instead of the acid chlorides. A preferred acid chloride is phosgene.

The reactants may be introduced into the reaction in any order. As a rule it is advantageous to start with the bisphosphinic acid derivatives II and thereafter to introduce the acid chlorides or bromides. The reaction of the bisphosphinic acid salts must be effected in the presence of inert solvents, of which chlorinated hydrocarbons, such as chloroform, methylene chloride, chlorobenzene, dichlorobenzene, etc. are preferred. The reaction of the free bisphosphinic acids and bisphosphinic acid esters does actually not require the use of solvents. However, for technical reasons their application may be advantageous.

The reaction is effected in a way that the bisphosphinic acid derivative II and the acid halide are used in a molar ratio of about 1:1, a small excess amount of acid halide not being critical, as it contributes to effect a complete reaction.

A larger excess amount is not advantageous, since the bisphosphinic acid anhydrides I formed react with the excess acid halide to give the bisphosphinic acid halides. If these halides are formed as by-products, they may be hydrolyzed again, by adding a calculated amount of water, to yield the bisphosphinic acid anhydrides I.

In principle, the reactions may already be effected at room temperature, however, it is often advantageous to operate at a temperature of from about 50° to 250° C., preferably from about 100° to 200° C. When the bisphosphinic acid alkyl esters are used approximately at room temperature, the corresponding alkyl halides are obtained as by-product. Short-chain alkyl halides escape in a gaseous form and have no influence on the reaction material. However, alkyl halides having a longer chain, such as butyl chloride, may cause the anhydrides formed to precipitate, so that the reaction process is disturbed by the separation of phases taking place. This is why it is advantageous to operate at higher temperatures in cases where the higher alkyl halides formed are distilled off. If the proces is not carried out with the use of solvents, it is necessary to choose a reaction temperature which is above the solidification point of the final product, at the latest towards the end of the reaction.

After the reaction has been completed the final products are obtained in vacuo in a largely pure form, by known measures for the separation of solvents and/or by-products which may have remained in the reaction material, for example, by blowing out with inert gas (for example, nitrogen) or by distilling, optionally through initial distillation. The yields are practically quantitative. Since a purification of the final products can only be effected with difficulty, pure starting products should be used.

The anhydrides thus obtained are generally present in the form of linear polymers, whose polymerization degree—which has been designated by m in formula I—is unknown. The final groups of the polymer chain are probably closed by hydrogen and hydroxyl. In special cases, cyclic compounds may also be present.

The bisphosphinic acid anhydrides of the invention are used as comonomers in the preparation of plastic materials, for example polymers, polycondensates or polyaddition products; there are to be mentioned above all polyesters, especially linear polyesters, such as those of terephthalic acid, to which they impart good flame-retarding properties, but also improved dyeing properties (cf. U.S. Pat. No. 3,962,194). However, the novel compounds ,ay be used in particular as intermediate products for the preparation of flame proofing agents for fibrous material (cf. U.S. application Ser. No. 913,083).

The following Examples are to serve the further illustration of the invention, without limiting its scope.

EXAMPLE 1

211 Grams of methane-bis-(methylophosphinic acid-isopropyl ester) are heated to 100° C. Thereafter about 100 g of phosgene are introduced in a gaseous form within 3 hours, while stirring vigorously, the internal temperature being increased to 190° C. during this process. At the same time the isopropyl chloride formed is distilled off. Upon completion of the reaction, nitrogen is passed through the reaction material for 2 hours at 190° C. The remaining volatile components are then eliminated in the water jet vacuum in the course of 1 hour at 190° C. 127 Grams of methane-bis-(methylphosphinic acid)-anhydride are obtained which has a solidification point of about 150° C. The product is insoluble in chloroform. The yield is 100% of the theory.

EXAMPLE 2

300 Grams of ethane-1,2-bis-(methylphosphinic acid-isobutyl ester) are heated to 160° C. Subsequently phosgene is passed through the above substance for 3 hours, while stirring vigorously. In the course of the reaction the isobutyl chloride formed is distilled off. Upon completion of the reaction, nitrogen is blown through the mixture during 6 hours at 170° C. 169 Grams of ethane-1,2-bis-(methylphosphinic acid)-anhydride are obtained which has a solidification point in the range of from about 115° to 120° C. The product is soluble in chloroform. The yield is 100% of the theory.

In the 1H-NMR spectrum recorded with the Varian-T60 spectrometer at a measuring frequency of 60 MHz in CDCl₃ as solvent with the reference substance tetramethylsilane (TMS) as internal standard, the following signals were found:
$\delta CH_3$: 1.9 ppm ($J_{PH}$=15 Hz)
$\delta CH_2$: 1.5 to 3 ppm

EXAMPLE 3a

580 Grams of methane-phosphonous acid-n-butyl ester are heated under a nitrogen atmosphere to 165° C. Subsequently a mixture of 175 g of hexadiene-1,5 and 3 g of ditert.-butyl peroxide are introduced dropwise in the course of 2 hours, while stirring vigorously, and stirring is continued for 1 hour at this temperature. Thereafter the mixture is distilled at 6.5 mbars to an internal temperature of 170° C.

There remain 655 g of hexane-1,6-bis-(methylphosphinic acid-n-butyl ester). This corresponds to a yield of 87% of the theory.

EXAMPLE 3b

701 Grams of hexane-1,6-bis-(methylphosphinic acid-n-butyl ester) are heated to 130° C. Thereafter 220 g of phosgene are introduced in a gaseous form within 5 hours, while stirring vigorously, and subsequently nitrogen is blown through the mixture for 2 hours. In the course of this process n-butyl chloride is distilled off. Afterwards the mixture is heated to 180° C. and is maintained at this temperature for 4 hours in the water jet vacuum.

There remain 442 g of hexane-1,6-bis-(methylphosphinic acid)-anhydride having a solidification point in the range of from about 55° to 60° C. The product is soluble in chloroform. The yield is about 100% of the theory.

In the 1H-NMR spectrum recorded with the Varian T60 spectrometer at a measuring frequency of 60 MHz in CDCl₃ as solvent with the reference substance TMS as internal standard, the following signals were found:
$\delta CH_3$: 1.9 ppm ($J_{PH}$=15 Hz)
$\delta CH_2$: 1 to 3 ppm

EXAMPLE 4

394 Grams of decane-1,10-bis-(methylphosphinic acid) are heated to a temperature of from 130° to 140° C. Thereafter 150 g of phosgene are introduced within 4 hours. Subsequently the mixture is heated to 180° C., and a water jet vacuum is established for 6 hours.

There remain 370 g of decane-1,10-bis-(methylphosphinic acid)-anhydride having a solidification point of from about 20° to 25° C. The product is soluble in chloroform. The yield is 100% of the theory.

In the 1H-NMR spectrum recorded with the Varian T60 spectrometer at a measuring frequency of 60 MHz in CDCl₃ as solvent with the reference substance TMS as internal standard, the following signals were found:
$\delta CH_3$: cannot be determined $\delta CH_2$: 1 to 3 ppm

EXAMPLE 5

39 Grams of p-phenylene-bis-(methylphosphinic acid-ethyl ester) are heated to 180° C., and phosgene is slowly introduced, while stirring. In the course of 1.5 hours the temperature is increased to 230° C. Subsequently nitrogen is passed through the mixture at this temperature. 29 Grams of p-phenylene-bis-(methylphosphinic acid)-anhydride are obtained which have a solidification point in the range of from about 190° to 200° C. The product is soluble in chloroform. The yield is 100% of the theory.

In the 1H-NMR spectrum recorded with the Varian-T60 spectrometer at a measuring frequency of 60 MHz in CDCl₃ as solvent with the reference substance TMS as internal standard, the following signals were found:
$\delta CH_3$: 1.85 ppm and 2.1 ppm ($^2J_{PH}$: 13 to 14 Hz)
$\delta arom$: 7.5 to 8.5 ppm

EXAMPLE 6

44 Grams of p-xylylene-bis-(methylphosphinic acid) are heated to 240° C., and phosgene is slowly introduced, while stirring. In the course of 1.5 hours the temperature is reduced to 210° C. Subsequently nitrogen is passed through the mixture at this temperature. 41 Grams of p-xylylene-bis-(methylphosphinic acid)-anhydride are obtained which have a solidification point of from about 165° to 175° C.

The product is soluble in chloroform. The yield is 100% of the theory.

In the 1H-NMR spectrum recorded with the Varian-T60 spectrometer at a measuring frequency of 60 MHz in CDCl₃ as solvent with the reference substance TMS as internal standard, the following signals were found:
$\delta CH_3$: 1.25 to 2.25 ppm
$\delta CH_2$: 2.9 to 4 ppm
$\delta arom$: 6.8 to 7.5 ppm

EXAMPLE 7

200 Grams of propane-1,3-dimethyl-phosphinic acid are heated to 170° C., and the amount of phosgene required for the reaction is slowly introduced, while stirring. Upon completion of the reaction the hydrogen chloride present in the reaction mixture is eliminated in the water jet vacuum at 140° C. The residue is distilled. 175 Grams of propane-1,3-dimethyl-phosphinic acid-anhydride are obtained which corresponds to the formula shown below and has a melting point of from 122° to 130° C. and a boiling point of 163° C. at 4.9 mbars. This corresponding to a yield of 96% of the theory.

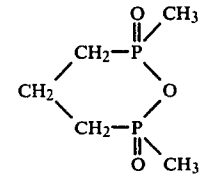

What is claimed is:
1. Bisphosphinic acid anhydrides of the formula

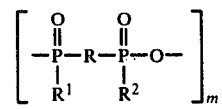

in which R is a saturated, open-chain branched or unbranched alkylene radical having from 1 to 10 carbon atoms,

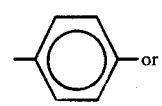-or

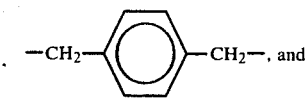

$R^1$ and $R^2$ represent identical or different alkyl groups having from 1 to 4 carbon atoms and m is an integer of greater than or equal to 1.

2. Bisphosphinic acid anhydrides of the formula

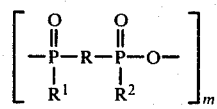

in which R is a saturated unbranched alkylene radical having from 1 to 10 carbon atoms,

$R^1$ and $R^2$ represent identical alkyl groups having from 1 to 4 carbon atoms and m is an integer of greater than or equal to 1.

3. Bisphosphinic acid anhydrides of claim 1 or 2 wherein the number of carbon atoms in R is 1 to 6.

4. Bisphosphinic acid anhydrides of claim 1 or 2 wherein the number of carbon atoms in $R^1$ and $R^2$ is 1 to 2.

* * * * *